United States Patent [19]
Dalke et al.

[11] Patent Number: 6,071,258
[45] Date of Patent: Jun. 6, 2000

[54] PERFUSION CONTROL ASSEMBLY WITH IMPROVED COMPONENT VISIBILITY AND ACCESSIBILITY

[75] Inventors: William D. Dalke, Aurora; Gary A. Gruszecki, Arvada, both of Colo.

[73] Assignee: COBE Cardiovascular, Inc., Arvada, Colo.

[21] Appl. No.: 08/304,725

[22] Filed: Sep. 12, 1994

[51] Int. Cl.[7] ............................. A61M 37/00; A61M 1/14
[52] U.S. Cl. ................................. 604/5; 604/19; 604/259; 600/16; 422/44; 422/45
[58] Field of Search ................................. 600/16; 422/44, 422/45; 435/48, 283, 283.1; 128/DIG. 3; 604/4, 5, 113, 114, 27, 29, 19, 259; D24/185

[56] References Cited

U.S. PATENT DOCUMENTS

| | | | |
|---|---|---|---|
| D. 230,716 | 3/1974 | Cerenowicz et al. | D24/185 |
| D. 241,549 | 9/1976 | Rota | D24/185 |
| 3,536,451 | 10/1970 | Ludwin | 422/45 |
| 3,545,221 | 12/1970 | Swenson et al. | 435/283 X |
| 4,411,786 | 10/1983 | Russell | 604/5 X |
| 4,490,331 | 12/1984 | Steg | 422/46 |
| 5,069,661 | 12/1991 | Trudell . | |
| 5,228,791 | 7/1993 | Fort | 400/489 |
| 5,270,005 | 12/1993 | RAible | 422/46 |
| 5,308,320 | 5/1994 | Safar et al. | 604/4 |
| 5,385,540 | 1/1995 | Abbott et al. | 604/4 |
| 5,391,142 | 2/1995 | Sites et al. | 604/4 |
| 5,403,281 | 4/1995 | O'Neill et al. | 604/113 |

FOREIGN PATENT DOCUMENTS

| | | | |
|---|---|---|---|
| 9204060 | 3/1992 | WIPO | 604/4 |

OTHER PUBLICATIONS

Medtronic Bio–Medicus, "Bio–Medicus PBS™ Cabinets", (1992).
Medtronic, "The Bio–Medicus PBS", (1991).
Ernest J. McCormick, *Human Factors Engineering Third Edition*, Chapter 13, pp. 415–435 (McGraw–Hill 1970).
16 photographs of Pemco System, taken Oct. 6, 1994.
COBE Personalized Perfusion Products Components Catalog, pp. 5–6 (1989).
Ernest J. McCormick, *Human Factors Engineering Third Edition*, Chapter 12, pp. 385–413 (McGraw Hill 1970).
Galletti, P.M. (1993) Artif. Organs 17(8):675–686.
Nose, Y. (1989) Artif. Organs 13(2):89–90.
Rygg. I.H. et al. (1976), pp. 139–146 in Ionescu, M.I. Current Techniques in Extracorporeal Circulation, Great Britain.

*Primary Examiner*—Mark O. Polutta
*Attorney, Agent, or Firm*—Popovich & Wiles, PA

[57] ABSTRACT

An improved perfusion control assembly comprising a console and an oxygenator flanked by at least two flanking units, wherein a first flanking unit is a pump assembly and additional flanking units are at least one of additional pump assemblies, a display monitor, a parameter monitoring assembly, or a controller, is described. The improved assembly can have the advantages of a reduced extracorporeal blood volumes in cardiopulmonary and cardioplegia circuits, and improved ergonomics for the perfusionist. In a preferred embodiment, the elongated console of the assembly is divided into a central and at least two peripheral segments connected by hinged joints. The perfusionist may rotate segments to create a cockpit shaped assembly.

45 Claims, 5 Drawing Sheets

FIG.6

PERFUSION CONTROL ASSEMBLY WITH IMPROVED COMPONENT VISIBILITY AND ACCESSIBILITY

FIELD OF THE INVENTION

The subject invention relates to a perfusion control system which has improved operator access to its oxygenator, pump modules, fluid tubing and other components. The improved perfusion control system has particular applicability in open-heart surgery.

BACKGROUND OF THE INVENTION

Open-heart surgery usually requires the use of a system for the extracorporeal circulation of fluids through a number of fluid circuits. These fluid circuits typically include a cardiopulmonary circuit, a cardioplegia circuit, a cardiotomy circuit and a ventricular vent circuit. The circuit tubing, pumps and related instrumentation and support console are referred to as a perfusion control system or a heart-lung machine.

The cardiopulmonary circuit, which is designed to functionally replace or supplement the heart and lungs during heart surgery, comprises one or more pumps for blood circulation and an oxygenation device. In prior art systems such as the COBE® Perfusion Control Assembly, a catheter receives blood from a major vessel entering the heart (e.g., vena cava) and the blood is directed through a venous line to a blood reservoir, through a cardiopulmonary loop to an oxygenator, and then back to the patient through an arterial line to a catheter in a major vessel leaving the heart (e.g., aorta). Either the arterial line or cardiopulmonary loop has a pump disposed thereon; the venous line may have a pump disposed thereon. It is generally desirable to have the cardiopulmonary circuit (both arterial and venous lines) be as short as safely possible to reduce priming volume and extracorporeal blood volume, blood dilution and inadequate oxygenation, and to minimize the need for transfusions and the attendant risk of blood-borne infections (e.g., HBV, HCV, or HIV). The cardiopulmonary pump on the cardiopulmonary loop or arterial line (sometimes referred to as the arterial pump) is used to pump blood from the reservoir through an oxygenation device. The reservoir is often positioned at a level below that of the patient on the operating table so as to permit gravitational drainage from the patient into the venous line. The blood is then pumped through an oxygenator and then an arterial line and another catheter into a major vessel exiting the heart. The cardiopulmonary circuit may include other devices such as a bubble detector on the arterial line to guard against bubbles entering the bloodstream; microemboli filters on the arterial line to prevent thromboemboli or gas emboli from entering the bloodstream; a timer to record the duration of extracorporeal blood circulation; temperature sensors and heat exchangers to monitor and control the temperature of the circulated blood; pressure transducers to monitor the pressure in the extracorporeal circuit; and devices to monitor blood characteristics such as the hemoglobin, oxygen saturation level, hematocrit, pH and blood gases. The cardiopulmonary pump can be a peristaltic, centrifugal, bladder or other pump, and it may be operable in a steady and continuous manner or in a pulsatile manner to mimic the beating of the heart.

The cardioplegia circuit delivers cardioplegia to the heart. Cardioplegia reduces or discontinues the beating of the heart in a manner that will minimize damage to the myocardium. Cardioplegia can also supply other ingredients to provide for myocardium protection. Cardioplegia may be the crystalloid solution (KCl, sugars, dextrose, magnesium, etc.) alone or may include oxygenated blood diverted from the arterial line. The cardioplegia circuit comprises the oxygenated blood line, the crystalloid solution bag and line, the cardioplegia delivery line, a pump (e.g., peristaltic), and may also comprise pressure transducers to monitor the solution pressure, an air detector and filters to prevent bubbles from entering the heart, a timer, temperature sensors and a heat exchanger to monitor and control fluid temperature, and a device for controlling and recording the total volume of crystalloid solution that is pumped. The cardioplegia is delivered to the coronary arterial network or coronary sinus for distribution throughout the myocardium. The cardioplegia is then distributed through the circulatory system, or may occasionally be drawn out of the chest cavity and discarded or directed via the cardiotomy line to the cardiopulmonary circuit, as discussed immediately below.

The cardiotomy circuit is used to withdraw or suction blood or blood mixed with other fluids from the opened heart or the chest cavity and deliver it to the cardiopulmonary circuit. The cardiotomy circuit typically comprises a suction tip, a fluid line, a pump (e.g., peristaltic), and a reservoir, and may comprise a filter disposed in the fluid line. The filter functions to remove foreign material picked up by the suction tip of the cardiotomy circuit. The cardiotomy reservoir may be the same as the cardiopulmonary blood reservoir. In addition to storing suctioned blood, the cardiopulmonary and cardiotomy reservoirs can also function to filter and defoam the blood.

The ventricular vent circuit functions to drain the left ventricle of blood that returns via the bronchial artery and pulmonary veins. Drainage from the pulmonary system, the coronary venous system and backflow from the aorta to the left ventricle can overfill the ventricles during bypass surgery. Such distention can stretch muscle fibers and weaken them. The ventricular vent circuit typically comprises a cardiac catheter inserted into the left ventricle, tubing, a pump (e.g., peristaltic), and a reservoir. The vent circuit reservoir may be combined with the cardiotomy and cardiopulmonary blood reservoirs.

In addition to the foregoing, auxiliary pumps may also be provided as back-up pumps in the event of failure of the cardiopulmonary, cardioplegia, cardiotomy or vent pumps during surgery.

Existing systems for extracorporeal circulation or perfusion systems are commonly mounted on a wheeled console for convenient storage, transport and use. The typical mounting configuration includes a vertical or horizontal row of discrete units. The units can be pump assemblies (cardiopulmonary, cardioplegia, cardiotomy, vent or auxiliary pump) or a controller unit. The pump assembly typically comprises a pump housing which contains the actual pumping elements, such as a rotor with a set of rollers to engage the flexible tubing through which the pumped fluid flows and a raceway to hold the flexible tubing in place, and the pump motor and other mechanical components. The pump assembly also may comprise an instrumentation panel which could include pump controls such as power switches, speed adjustments and indicators, and forward and reverse controls. The controller unit can monitor pressure and temperature probes, bubble sensors and reservoir level sensors, regulate pump speeds, and transmit monitored information to a display. Pump assembly and controller units can be detachable and modular.

The wheeled console commonly has a number of accessories and a structure for attachment of the accessories. The structure may include one or more vertical poles or masts, a mounting crossbar and brackets for hanging or attaching fluid reservoirs, accessory instrumentation (e.g., a display), writing surfaces, bubble detectors, temperature sensor readouts and other desired devices. The oxygenator is typically mounted on a mast or crossbar.

The physical arrangement of fluid lines, pumps, reservoir, oxygenator and other components of the fluid circuits is important for proper operation of the perfusion system. It is generally considered important to have an arrangement that reduces the extracorporeal volume of all blood-containing circuits so as to reduce the need for transfusion or dilution. Additionally, the physical arrangement should be such that the perfusionist can scan, take samples, and consistently be aware of the status of all equipment, systems, and patient parameters. Adjustment of ventilation gases and administration of drugs can be based on observations made by the perfusionist. Once cardiopulmonary bypass has begun, the perfusionist must observe and regulate pump flow rates, check the color of and pressure in the arterial line, observe the blood level in the reservoir(s) to assure a steady state or balanced flow in and out, observe tubing for air in the lines, leaks or kinking, and regulate heat exchanger temperature to induce system hypothermia to the desired level. It is highly desirable that the perfusionist be able to observe the surgical team and operating table, and to observe and have direct access to the oxygenator, the fluid lines, the pumps, the reservoirs, etc. from a single standing or sitting position. For example, if the perfusionist observes that the blood level in the cardiopulmonary reservoir is rising due to an excessive venous return, he can adjust a clamp on the venous return line to slow the blood flow into the extracorporeal circuit and stabilize the blood level in the reservoir. In another example, the perfusionist, upon observing or learning of the premature reinitiation of the patient's heart beat (i.e., prior to termination of open-heart surgery), may adjust the cardioplegia pump or a clamp on the cardioplegia delivery line to increase the crystalloid concentration to the heart.

Historically, i.e., in the 1950's, bubble oxygenators (membrane oxygenators were not invented until the 1960's) were located behind a console comprising cardioplegia and cardiopulmonary pumps. An example of this design is the Rygg-Kyvsgaard heart-lung machine manufactured by Polystan (described in Rygg, I. H. et al., "The Rygg-Kyvsgaard Pump-Oxygenator" in Ionescu, M. I. (1976) Current Techniques in Extracorporeal Circulation, Butterworth & Co., Great Britain). It was necessary to place the oxygenator behind the pumps because it was a large bag that could be extended only by mounting on a crossbar. The height of the oxygenator crossbar was adjusted to control the venous flow rate. Therefore, the oxygenator bag was often not completely visible to the perfusionist. The bubble or membrane oxygenators of the 1960's were smaller and the venous flow rate was controlled by a clamp on the venous line rather than by adjusting the height of the oxygenator. Consequently, the oxygenator was moved from behind the horizontal array of pumps to a peripheral position (i.e., to the left or right of the horizontal array) to improve accessibility and visibility. At this time there were still usually only two pumps located on the console. However, heart-lung machines became more complex over time with the addition of a cardiotomy pump, a ventricular vent pump, a central controller module, a display, temperature and pressure sensors, reservoirs, etc. By the 1970's, most manufacturers employed at least four pumps in a horizontal array with an oxygenator located peripherally. While the addition of new components to the perfusion control system improved its performance, such additions also increased the system's footprint, thereby creating perfusionist ergonomic issues. Specifically, the perfusionist would often have to shift positions to have access to each component of the system. Further, the larger footprint increased the perfusionist's routine visual circuit to monitor all components. For example, the perfusionist in some cases had to shift his stool or take one or more steps in order to obtain a clear view of a component. Thus, there has been a need since the 1970's for a perfusion assembly design that addresses these concerns. The expanding complexity of the heart-lung machine has been noted by skilled artisans in the field. See, e.g., Nosé, Y. (1989) Artif. Organs 13:89–90; and Galletti, P. M. (1993) Artif. Organs 17:675–86.

As discussed above, one currently existing extracorporeal circulation or perfusion assembly is the COBE® Perfusion Control System (sold by the assignee of the subject application), which features a horizontal row of pump modules and the Perfusion Controller module on the console; and the oxygenator, display, air emboli protection system, venous line occluding clamp, gas flow meter and halogen console lamp fastened to the masts or mounting crossbar. As described in copending U.S. Ser. No. 07/941,389, now SIR H1324, incorporated herein in its entirety by reference, which describes an alternative control system for the COBE Perfusion System, the control of the pumps in the horizontal array (referred to in SIR H1324 as "perfusion assemblies") may be via the local instrumentation panel or the controller unit. The oxygenator is adjustable on the mast via a swing arm, and can be swung approximately 270° about the mast axis from a position in which it is adjacent to an outside pump assembly in the horizontal array to a position where it is centrally located behind the horizontal row of modules. The latter position may reduce the length of the cardiopulmonary circuit, but frequently requires the perfusionist to move to obtain a clear view of the oxygenator and access for clamping or debubbling.

Other currently existing systems include the Sorin SIII™ Perfusion System, the Sarns® 8000 Perfusion System, the Polystan™ Heart-Lung Machine System, the Pemco™ system, and the Bard® Cardiopulmonary Support (CPS™) System. The Sorin Perfusion System also features a horizontal row of pump modules on the console, with a halogen console light, venous occlusion clamp and instrument stack for control and monitoring modules mounted on masts or mounting crossbars. The Sarns 8000 Perfusion System has a horizontal arrangement of its pumps, display, monitoring and control functions. The Polystan Heart-Lung Machine System comprises a horizontal row of pumps on a console, a horizontal modular monitoring rack mounted at eye level (which appears to obstruct a view of the operating table), a computer interface and communications port in its console base, masts or I.V. poles, and an IBM compatible program which collects and displays data accumulated from the monitors. The Pemco heart pump console can be customized to provide a horizontal or vertical arrangement of modular pumps. In the Sorin, Sarns, Pemco and Polystan systems, the oxygenator is peripherally mounted on a mast. The Bard cardioPulmonary Support system, which is designed for cardiopulmonary support in emergency situations, comprises an oxygenator centrally located between a pump and a heat exchanger.

SUMMARY OF THE INVENTION

The subject invention comprises an extracorporeal fluid perfusion assembly comprising a console, a central cavity adapted to receive an oxygenator, at least two units which sit atop the console and flank the central cavity, wherein said flanking units are defined as comprising at least one pump assembly and at least one of a controller, a pump assembly, a parameter monitoring assembly, or a display monitor. The dimensions of the central cavity accommodate an oxygenator, and may also accommodate a reservoir and heat exchanger. The reservoir is typically a single reservoir that receives inflow from the venous line, the cardiotomy line and the vent line.

The pump assembly comprises a housing with pump means and an instrument panel for optional local control of the pumping means. The pump assemblies can be controlled via their local instrument panels or via the controller. The pumping assemblies include the cardiopulmonary, cardioplegia, ventricular vent and cardiotomy pumps. A parameter monitoring assembly is an assembly that monitors and may display patient or blood parameters, including without limitation blood gases, arterial and venous oxygen saturation, hematocrit, anticoagulation time, pH, hemoglobin, electrolytes (potassium, sodium, calcium, etc.), temperature, pressure, reservoir blood level and cardioplegia line and arterial line air bubbles. The monitoring assembly may also monitor and regulate the composition of feed gases ($O_2$, $CO_2$ and $N_2$) conveyed to the oxygenator, or may regulate a venous clamp for controlling flow from the patient to the reservoir or oxygenator. The controller can collect and monitor input from the parameter monitoring assembly, from other temperature or pressure sensors, or bubble or reservoir level detectors or the like, transmit that information to the display monitor for display, and may process the information to regulate pump assemblies. As used herein, a parameter monitoring assembly can measure, monitor and display parameters; in contrast, the controller receives information from monitoring assemblies or other sensors or detectors, processes such information, and transmits the information for display. However, it is to be understood that the functions of controller and parameter monitoring assembly can be exchanged or combined in a single unit.

While it is contemplated that the flanking units can include a display and a controller, it is also possible that the controller could be housed elsewhere in the assembly, such as in the console, and that the display monitor could be mounted on a mounting fixture (described hereinbelow).

The flanking units can be detachable and positionally interchangeable. That is, the flanking units may be designed so that any one unit is positionally exchangeable with another. The console may be elongated, and can be substantially rectangular. The console may be divided into a central segment and peripheral segments whose joints can be hinged. The central cavity is positioned above the central segment of the console, and the flanking units are positioned atop the peripheral segments. The central segment can be a console crossbar that joins the two front surfaces of the peripheral segments. The length of the central segment may be adjustable by telescoping means, or by substitution with crossbars of different length. In one embodiment, the console's peripheral segments comprise sets of steps rising from the front surface to the back surface of the console or assembly. In this embodiment, the flanking units can be positioned on the steps. In a second embodiment, the flanking units are vertically stacked. A preferred variation of this second embodiment has the stacked units canted and offset from units immediately below so that the front surface of each flanking stack slants toward the back surface of the assembly as the stacks ascend. This provides an angled surface that permits the perfusionist to directly observe the instrument panels and raceways of the pump assemblies. In either of the foregoing embodiments, the multiple pumping assemblies can be positioned to be radially equidistant from the vertical oxygenator axis; minimization of this radius may reduce total extracorporeal volume.

The assembly can also have mounting fixtures, such as masts or I.V. poles and mounting crossbars. The mounting crossbars may contain telescoping means to permit expansion or contraction during adjustment of the length of the central segment of the console and during rotation of the peripheral segments about their joints with the central segment.

The assembly can further comprise a cardiopulmonary circuit (venous line, cardiopulmonary pump loop, and arterial line), a cardiotomy circuit, a ventricular vent circuit, and a cardioplegia circuit (crystalloid solution supply line, cardioplegia blood line and cardioplegia delivery line). Cardioplegia or crystalloid solution may be heated or cooled in a heat exchanger such as the Kardia+ heat exchange device, described in U.S. Pat. No. 5,269,749, sold by the assignee of the subject application. Monitoring systems, such as air bubble detectors on the arterial or cardioplegia delivery lines, level detectors and temperature sensors on the reservoir, pressure sensors on the venous, arterial, cardioplegia delivery or vent lines, or temperature sensors on the venous, arterial or cardioplegia delivery lines can be present. As mentioned above, these sensors and detectors can be monitored by the controller.

The subject invention also contemplates a method for extracorporeal oxygenation of blood of a patient by employing an apparatus with a plurality of units which flank an oxygenator, wherein the units include a first pump assembly and at least one other unit such as a pump assembly, a parameter monitoring assembly, a display monitor or a controller. At a minimum, the method involves the operation of the first pump assembly as a cardiovascular pump, whereby blood is pumped from the patient through a venous line to the oxygenator and back to the patient through an arterial line. In being transported from the venous line to the oxygenator, the blood may optionally flow through a reservoir. The method can additionally include the operation of a second pump assembly which pumps crystalloid solution in the crystalloid solution supply line and oxygenated blood in the cardioplegia blood line to the composite cardioplegia delivery line, and thereafter into the patient. The method can additionally include operating a third pump assembly which pumps the blood and other fluids in the patient's chest cavity to the oxygenator, possibly by way of the reservoir. The method can further include the operation of a fourth pump assembly which pumps blood from the left ventricle of the patient to the oxygenator, possibly by way of the reservoir. In addition to operation of pumping assemblies, the subject method can also include the operation of other flanking units, such as a parameter monitoring assembly, a display monitor and/or a controller.

In another embodiment, the inventive method comprises employing an assembly of first and second pump assemblies that flank an oxygenator that is centrally located on a console. This method involves the following steps: draining the blood from the patient to the oxygenator; oxygenating the blood in the oxygenator; pumping (pump assembly one) a first portion of the oxygenated blood to flow back to the patient; pumping (pump assembly two) and combining the second portion of the oxygenated blood and crystalloid solution to make cardioplegia; and permitting the cardioplegia to flow to the patient.

The subject arrangement of components has many advantages over existing assemblies. First, there is a potential reduction of the extracorporeal volume of one or more blood lines by the centralized oxygenator design, thereby reducing the need for transfusions, blood dilution and large priming volumes. In particular, the pump heads may be arranged in a radially equidistant fashion about the vertical oxygenator axis as described hereinbelow; provided that the radius is relatively short, this arrangement can reduce extracorporeal volume of several lines. An additional advantage of the subject design is that it can facilitate the perfusionist's observation of and access to all components of the assembly, including the oxygenator, the blood and fluid lines, pump assemblies, the reservoir, and the display monitor. Virtually all equipment can be visible from one position by using eye movement alone. Also, all flanking equipment can be within arm's length from a single position. Since the oxygenator and reservoir are at the center of the system, the perfusionist can devote more of his attention to them without losing sight of other important equipment. The improved visibility of blood lines is provided by the positioning of pump heads in columns or cascades that flank the oxygenator and distribute the tubing. In one embodiment, the visibility of the blood lines is further enhanced by canting of the pump assembly surfaces such that the operator has a direct view of the tubing in the raceways and the pump instrumentation from a seated position. These ergonomic advances can improve perfusionist efficiency. A further advantage of the subject apparatus is that it provides an unobstructed view of the operating table, operating room monitors and/or surgical team. By arranging the flanking units in two stacks or cascades rather than one, the bulk of the system is below the seated perfusionist's line of sight to the operating table. Yet another potential advantage of the subject design is that it may reduce back discomfort to the perfusionist as it may reduce the bending required to have a direct view of or access to the pump heads, tubing, instrumentation, oxygenator and reservoir.

DETAILED DESCRIPTION OF THE INVENTION

An understanding of the improvements and advantages of the subject invention is further elucidated from a description of the drawings.

Figure 1:
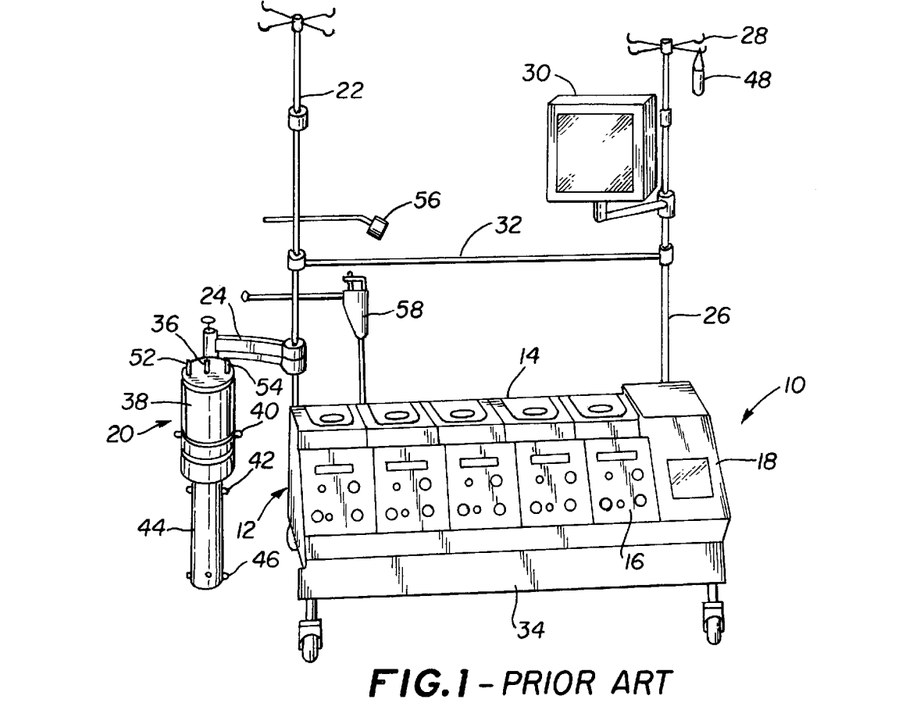
FIG. 1 is a pictorial view of a prior art extracorporeal circulation assembly having a horizontal row of function and control units.

FIG. 1 illustrates the COBE® Perfusion Control Assembly 10, a prior art assembly. It comprises a horizontal row of six modules: five are pump assemblies 12 comprising peristaltic pump heads 14 and an instrument control panel 16; the sixth is a central control module 18. An assembly of the oxygenator, heat exchanger and reservoir ("oxygenator assembly") 20 is mounted on a mast 22 with a swing arm 24.

At the top of each mast 22, 26 are hooks 28 for hanging of blood, saline solution, crystalloid solution or other fluids. A display monitor 30 is mounted on mast 26, and is electronically connected to the central control unit 18 by wiring outside mast 26. Mounting crossbar 32 provides additional scaffolding for hanging of writing surfaces, bubble detectors, and other desired devices. Arterial line bubble detector 56 can be disposed on mast 22. Venous line clamp 58, which can also be disposed on mast 22, is used to regulate venous flow to the reservoir 38 of the oxygenator assembly 20. Pump assemblies 12 can be under the local control of their instrument panel 16 or may be under the control of the central controller 18. Communication ports and wiring (not shown) in the console 34, on the masts 22, 26 or elsewhere, provide electrical communication with the central controller 18. The central controller 18 can receive information from an arterial bubble sensor 56, a blood level sensor in the reservoir (not shown), temperature sensors disposed in arterial or cardioplegia lines or in the patient (not shown), and pressure sensors disposed in the arterial, cardioplegia or left ventricle lines (not shown). The controller 18 processes such information and can communicate it to the monitor 30. The controller also can control the cardiopulmonary, cardioplegia and other pump heads 14. The central controller 18 and monitor 30 have keypads for perfusionist control of such functions or monitoring systems. The COBE Computerized Perfusion Controller Operator's Manual (May 1990), provides a complete description of the functions of the central controller 18.

Figure 2:
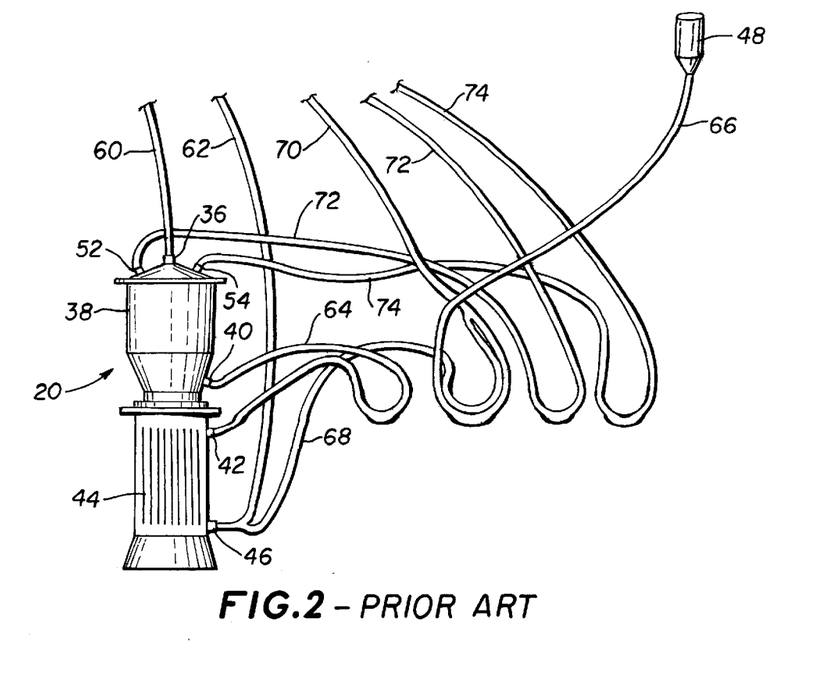
FIG. 2 is a front view of the oxygenator assembly and tubing arrangement corresponding to the assembly of FIG. 1.

For clarity, the tubing between the oxygenator assembly, pumps and patient have not been illustrated in FIG. 1. FIG. 2 is a pictorial schematic illustrating only the tubing and oxygenator assembly of the COBE Perfusion Control System. A venous line 60 which is connected to a major vessel entering the heart (not shown) transports blood from the patient to the venous port 36 of the reservoir 38. The cardiopulmonary pump loop 64 comprises a line connected to a second reservoir port 40 which is threaded through a peristaltic pump head 14 of a pump assembly 12 (FIG. 1), and which connects with a first oxygenator port 42 to transport blood from the reservoir 38 to the oxygenator 44. Usually, the cardiopulmonary loop is threaded through the pump head 14 of a pump assembly 12 (FIG. 1) immediately adjacent to the oxygenator assembly 20. The arterial line 62, connected to a "Y" adaptor off a second oxygenator port 46, transports the oxygenated blood to a major vessel exiting the heart (not shown). The crystalloid solution supply line 66, connected to a crystalloid solution supply bag 48, together with the cardioplegia blood line 68, connected to the other stem of the "Y" adaptor off oxygenation port 46, are threaded through another peristaltic pump head 14 of a pump assembly 12 (FIG. 1), and then combined into one line to produce a cardioplegia delivery line 70, which transports the cardioplegia to the heart (not shown). A cardiotomy line 72, which is threaded through another peristaltic pump head 14 of pump assembly 12 (FIG. 1), suctions blood and other fluids from the chest cavity (not shown) and transports it to a third reservoir port 52, whereby the fluid joins the cardiopulmonary circuit. Finally, a left ventricular vent line 74, which drains the left ventricle (not shown), is threaded through a fourth pump head 14 of a pump assembly 12, and transports blood to a fourth reservoir port 54, thereby relieving pressure in the ventricle. While the cardiopulmonary pump loop 64 is usually threaded through the pump head 14 of the nearest pump assembly 12 (so as to minimize volume in the cardiopulmonary circuit), the cardiotomy line 72, cardioplegia delivery line 70 and vent line 74 can be threaded through any of the remaining pump heads. It is also sometimes considered desirable to minimize the length of the cardioplegia blood line 68 and delivery line 70; therefore, the cardioplegia blood line 68 and crystalloid solution supply line 66 may be threaded through the next most adjacent pump head 14 (FIG. 1).

As can be appreciated by the foregoing description and FIG. 2, the physical arrangement of the eight fluid lines, five of which are threaded through pumps, and five of which are connected to the patient, require the careful attention of the perfusionist. Because the plurality of lines threaded through the five pump heads can droop behind the horizontal assembly of pumps, ergonomic issues arise regarding access to those lines and visual observation of each line for appropriate color, air bubbles, leaks or faulty connections. Additionally, the oxygenator assembly 20, and its multiple connections to the venous line 60, the cardiopulmonary pump loop 64, the arterial line 62, and the cardioplegia blood line 68, may not be plainly visible to the perfusionist from a single position, depending on the position of the oxygenator assembly 20 on the mast 22.

Figure 3:
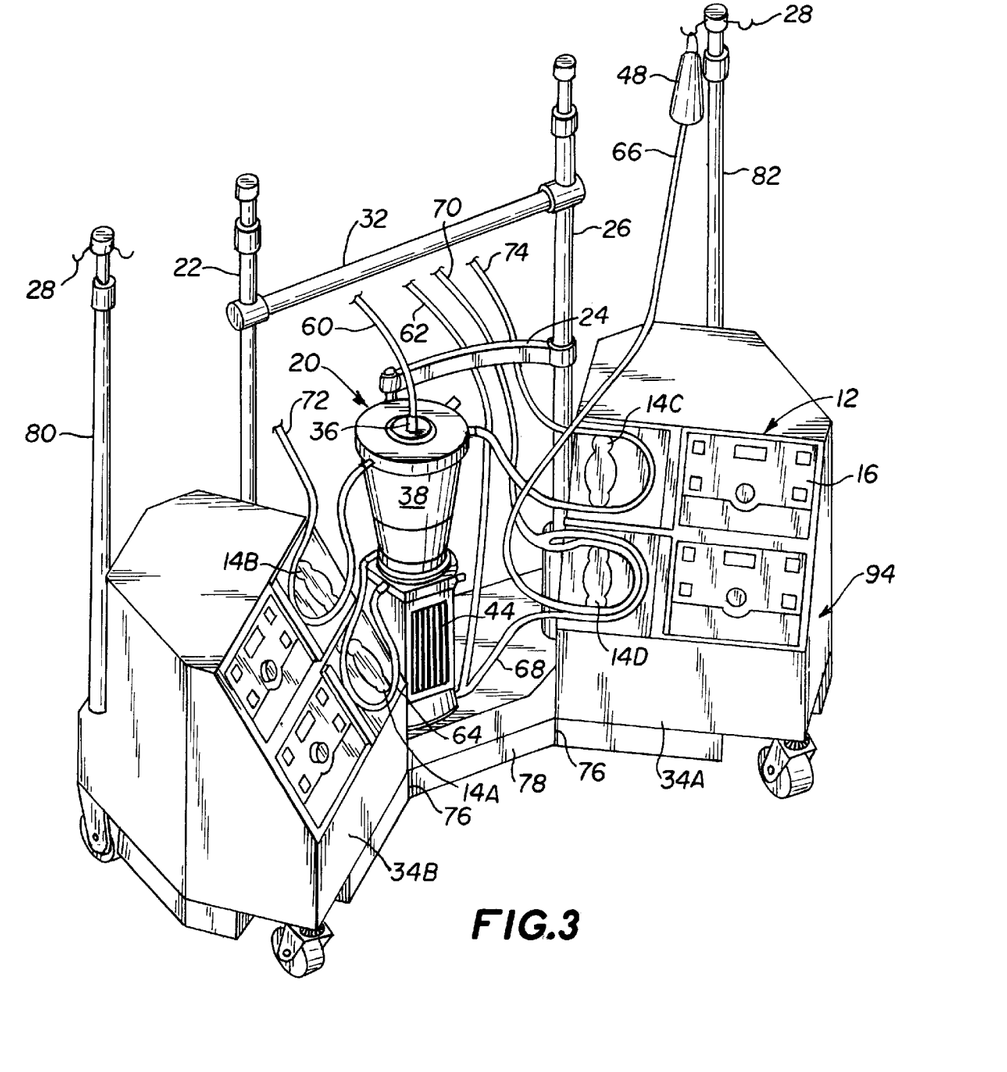
FIG. 3 is a pictorial view of a preferred embodiment of an extracorporeal circulation assembly of the subject invention.
Figure 5:
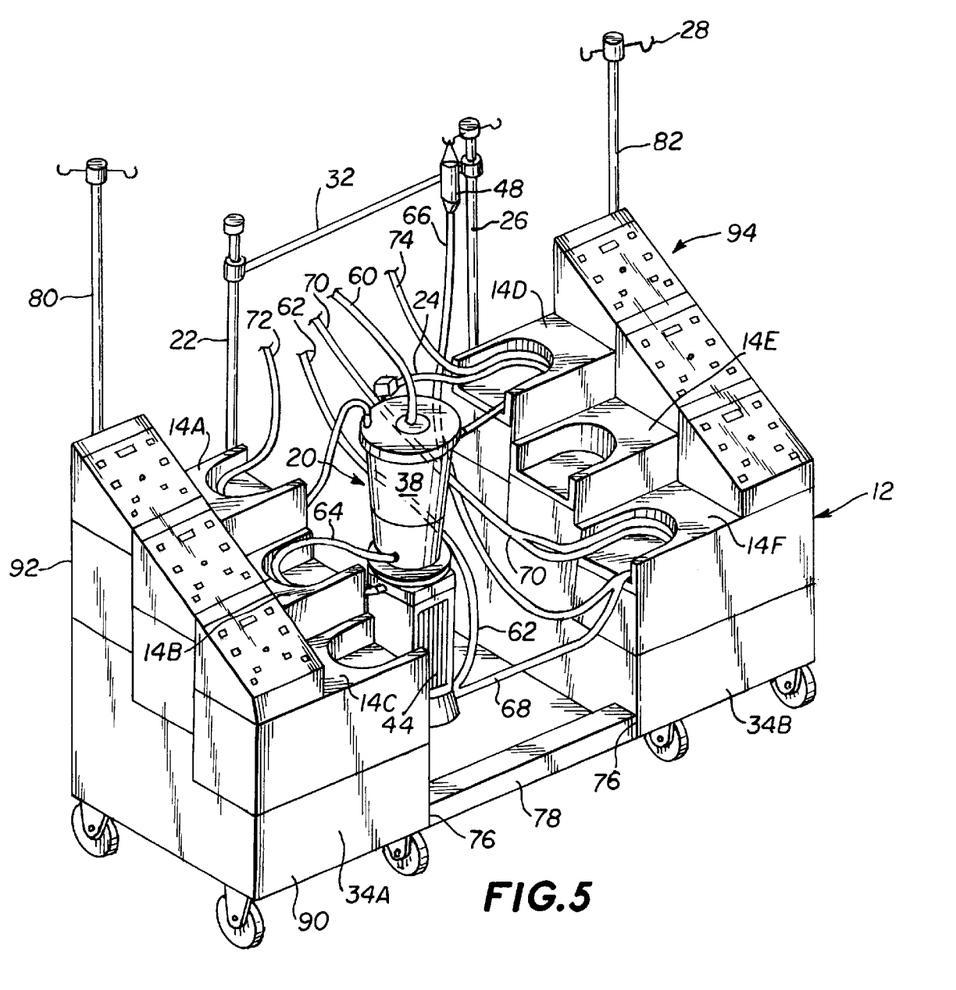
FIG. 5 is a pictorial view of a second embodiment of an extracorporeal circulation assembly of the subject invention.

In contrast, the subject inventive assemblies are designed to address these ergonomic issues and facilitate the perfusionist's tasks. FIG. 3 illustrates a p referred embodiment in which the oxygenator assembly 20 is located between flanking units 94 so as to create a centralized oxygenator design. In FIG. 3, certain details of the flanking units 94 have been omitted or simplified for clarity. The modular units 94 flanking the central oxygenator assembly 20 comprise at least one of a pump assembly 12, and may comprise one or more of a parameter monitoring assembly, a display monitor, and a controller. The pump assemblies 12 comprise a pump head (14A, B, C, D) and an instrument control panel 16. The subject invention contemplates at least two flanking units 94, the first of which is a pump assembly 12, and remaining of which are any of a pump assembly 12, a parameter monitoring assembly, a display monitor or a controller. FIG. 3 illustrates an embodiment in which all of the flanking units 94 are pump assemblies 12, the controller function is located in the console segments, 34A and B, and the display monitor could be mounted on mast 22, 26, 80, 82, or crossbar 32. As illustrated in FIG. 3, the pump assemblies 12 can be positioned such that the centers of their respective pump heads 14A–D are radially equidistant from the vertical axis of the oxygenator; provided the radii are relatively short, this arrangement may reduce tube volumes. Also, the pump assembly 12 surfaces can be canted so that the perfusionist can have a direct view of the tubing in the raceways from a seated position. The flanking units can be squarely stacked (not shown), stacked in a canted and offset manner to produce the pump assembly 12 front surface slant illustrated in FIG. 3, or positioned on a plurality of steps rising from the front surface of the console to the back surface (FIG. 5). While all of the units flanking the oxygenator assembly can be pump assemblies 12 as illustrated in FIG. 3, they may also include a parameter monitoring assembly, a display monitor and a central controller. The parameter monitoring assembly is a unit that measures a blood or patient parameter such as blood hematocrit, anticoagulation time, hemoglobin, pH, temperature, pressure, reservoir blood level, arterial or cardioplegia line air bubbles, electrolytes (potassium, sodium, calcium, etc.), venous or arterial oxygen saturation or blood gases. The parameter monitoring assembly may also comprise a venous clamp used to regulate flow to the oxygenator assembly, and may also monitor relative proportions of $O_2$, $CO_2$, and $N_2$ conveyed to the oxygenator. The oxygenator assembly 20 can be positioned between the flanking units by a swing arm 24. Hooks 28 are available for hanging crystalloid solution bags 48 or other bags or devices.

Figure 4:
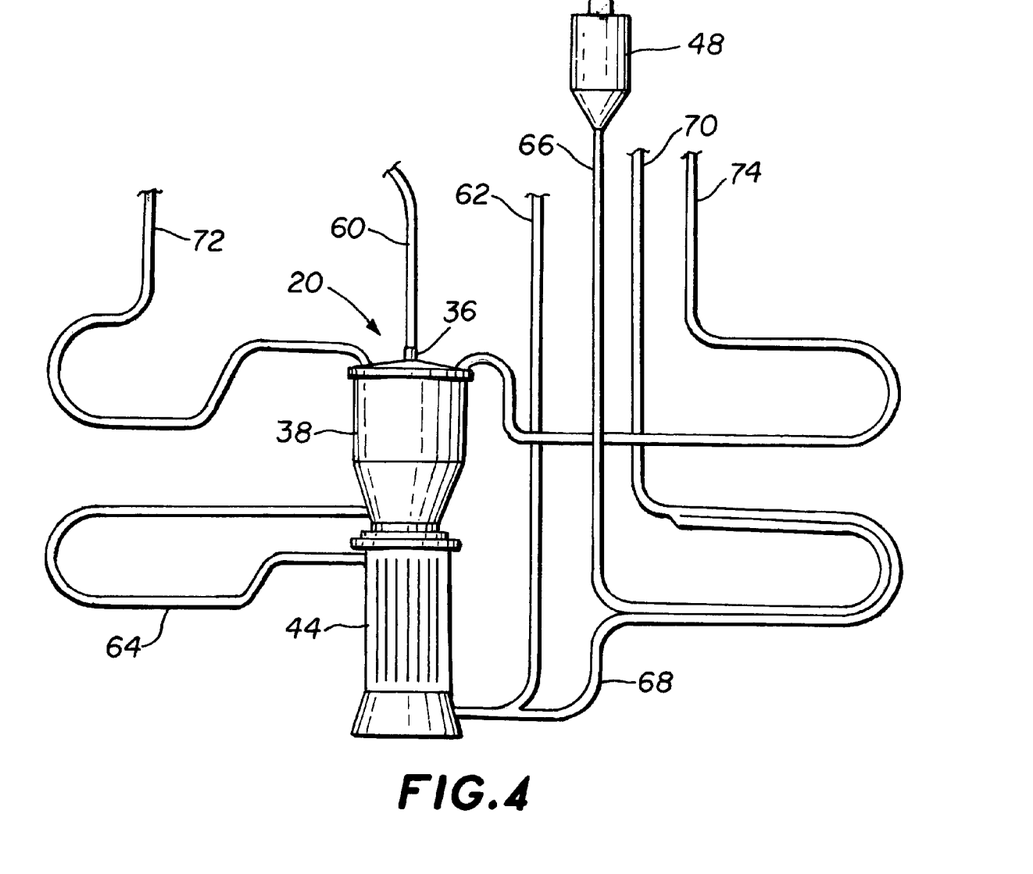
FIG. 4 is a front view of the oxygenator assembly and tubing arrangement corresponding to the assembly of FIG. 3.

The assembly of FIG. 3 represents a significant improvement over available perfusion assemblies in that the perfusionist, from a single position, can directly observe and have access to each flanking unit 94, the oxygenator 44 and the reservoir 38 of the oxygenator assembly 20, the venous line 60, the arterial line 62, the cardiopulmonary pump loop 64, the ventricular vent line 72, the cardiotomy line 74, the crystalloid solution supply line 66, the cardioplegia blood line 68, and the cardioplegia delivery line 70. For purposes of comparison with FIG. 2 (the prior art configuration of oxygenator assembly and tubing), FIG. 4 illustrates the oxygenator assembly and tubing of the preferred embodiment of FIG. 3. Referring to FIGS. 3 and 4, the venous line 60 transports blood from a large vessel entering the heart (not shown) to a venous port 36 of the reservoir 38. The blood can be heated by a heat exchanger (not shown) located in or outside the reservoir 38 and is transported via the cardiopulmonary pump loop 64 to the oxygenator 44. Although it is preferred that the cardiopulmonary pump loop 64 be threaded through adjacent pump 14A (FIG. 3) so as to minimize the cardiopulmonary circuit and reduce hemolysis, it may alternatively be threaded through more distant pump heads (14B, 14C, and 14D) of the assembly. The oxygenated blood is returned to a large vessel exiting the heart (not shown) via arterial line 62. A cardioplegia blood line 68, which transports oxygenated blood from the oxygenator 44, and crystalloid solution supply line 66 are threaded through pump 14D (or pumps 14A, B or C if desired) (FIG. 3). They are then combined via a "Y" adaptor to form cardioplegia delivery line 70, which conducts the cardioplegia to the coronary arterial network for distribution throughout the myocardium (not shown). Left ventricular vent line 72 transports blood from the left ventricle to the reservoir 38 via pump 14B (or pump 14A, C or D if desired) (FIG. 3). Cardiotomy line 74 is threaded through pump 14C (or through 14A, B or D if desired) (FIG. 3) to transport blood from the chest cavity to the reservoir 38.

A comparison of FIG. 2 (prior art) and FIG. 4 reveals an advantage of locating the oxygenator between flanking units: the fluid circuits and oxygenator assembly 20 are plainly visible to the perfusionist and directly accessible.

The flanking units 94 can be modular units that are interchangeable positionally, thereby allowing the perfusionist to build the assembly in a manner that most closely meets his needs. Additional flanking units 94, such as a second cardiotomy pump assembly or an auxiliary or backup pump assembly, can be positioned atop the illustrated modules of FIG. 3.

During an operation, the console is positioned so that the oxygenator assembly 20 is relatively close to the patient so as to minimize the cardiopulmonary circuit, yet does not obstruct access to the patient by the surgical team. The joints 76 of the console base can be hinged to permit the perfusionist to enclose himself within the lateral segments 34A, 34B of the console base, thereby creating a perfusionist "cockpit" having a U- or V-shape. Console crossbar 78 of the console base can comprise telescoping means to increase or decrease the distance between the lateral segments 34A and 34B of the console base. Likewise, mounting crossbar 32 can also comprise telescoping means so that the distance between masts 22 and 26 may be adjusted as lateral segments 34A and 34B are rotated about hinges 36 or as telescoping means within console crossbar 78 is adjusted. Thus, the perfusionist is permitted to expand or reduce the footprint of the assembly by adjusting swing arm 24, the length of console crossbar 78 and mounting crossbar 32, and hinged joints 76.

FIG. 5 illustrates a second embodiment of the subject invention which may be more suitable for perfusionists who stand during surgery. In FIG. 5, certain details of the flanking units 94 have been simplified or omitted for clarity. In the embodiment of FIG. 5, the flanking units 94 are positioned to create a cascade from the front surface 90 of the console to the back surface 92. The oxygenator assembly 20 is positioned between at least two flanking units 94. As discussed above, the flanking units 94 comprise a first pump assembly 12 and at least one of a parameter monitoring assembly, a display monitor, additional pump assemblies 12, and/or a controller. When all of the flanking units 94 are pump assemblies 12, the controller function can be situated in one or both of the lateral segments 34A, 34B of the console base, and the monitor can be secured to any of the four masts 22, 26, 80, 82 or the mounting crossbar 32. The oxygenator assembly can be positioned between flanking units with swing arm 24. Hooks 28 are available for hanging a crystalloid solution bag 48 or other bags or devices.

Like the assembly of FIG. 3, the assembly of FIG. 5 permits the perfusionist, from a single position, to directly access and observe each component. Venous line 60 transports blood from a major vessel entering the heart (not shown) to the reservoir 38, wherein the temperature of the blood is modified by contact with a heat exchanger located within or outside the reservoir 38. Cardiopulmonary pump loop 64, which is threaded through adjacent pump 14B (so as to minimize the volume and hemolysis in the cardiopulmonary circuit), then transports the blood from the reservoir 38 to the oxygenator 44. Arterial line 62 receives oxygenated blood from the oxygenator 44 and transports it to a major vessel exiting the patient's heart (not shown). Crystalloid solution supply line 66, which conveys crystalloid solution from crystalloid solution bag 48, and cardiopulmonary blood line 68 are both threaded through pump 14F, and are then combined to form the cardioplegia delivery line 70. The cardioplegia delivery line 70 then delivers the cardioplegia to the coronary arterial network for distribution throughout the myocardium (not shown). Ventricular vent line 72 transports blood from the left ventricle to the reservoir 38 via pump 14A. Cardiotomy line 74 is threaded through pump 14D and transports blood from the chest cavity to the reservoir 38. As discussed in reference to FIG. 3, the various circuit lines can be threaded through alternative pump heads. Further, the flanking units option ally can be interchangeable positionally so that the perfusionist can position the pump assemblies 12, controller, monitor, and/or parameter monitoring assembly as desired.

As with the assembly of FIG. 3, the console crossbar 78 and the mounting crossbar 32 may contain a telescoping means. The additional two flanking units 94 (i.e., as compared to FIG. 3) may comprise cardiotomy pumps or auxiliary, backup pumps. Console joints 76 can be hinged to permit positioning of the lateral segments 34A, 34B to form a U- or V-shape or cockpit. Again, the perfusionist can adjust the footprint of the assembly by adjusting the length of the mounting crossbar 32 and console crossbar 78, by rotating lateral segments 34A and 34B about hinges 76, and by positioning oxygenator assembly 20 via swing arm 24.

Figure 6:
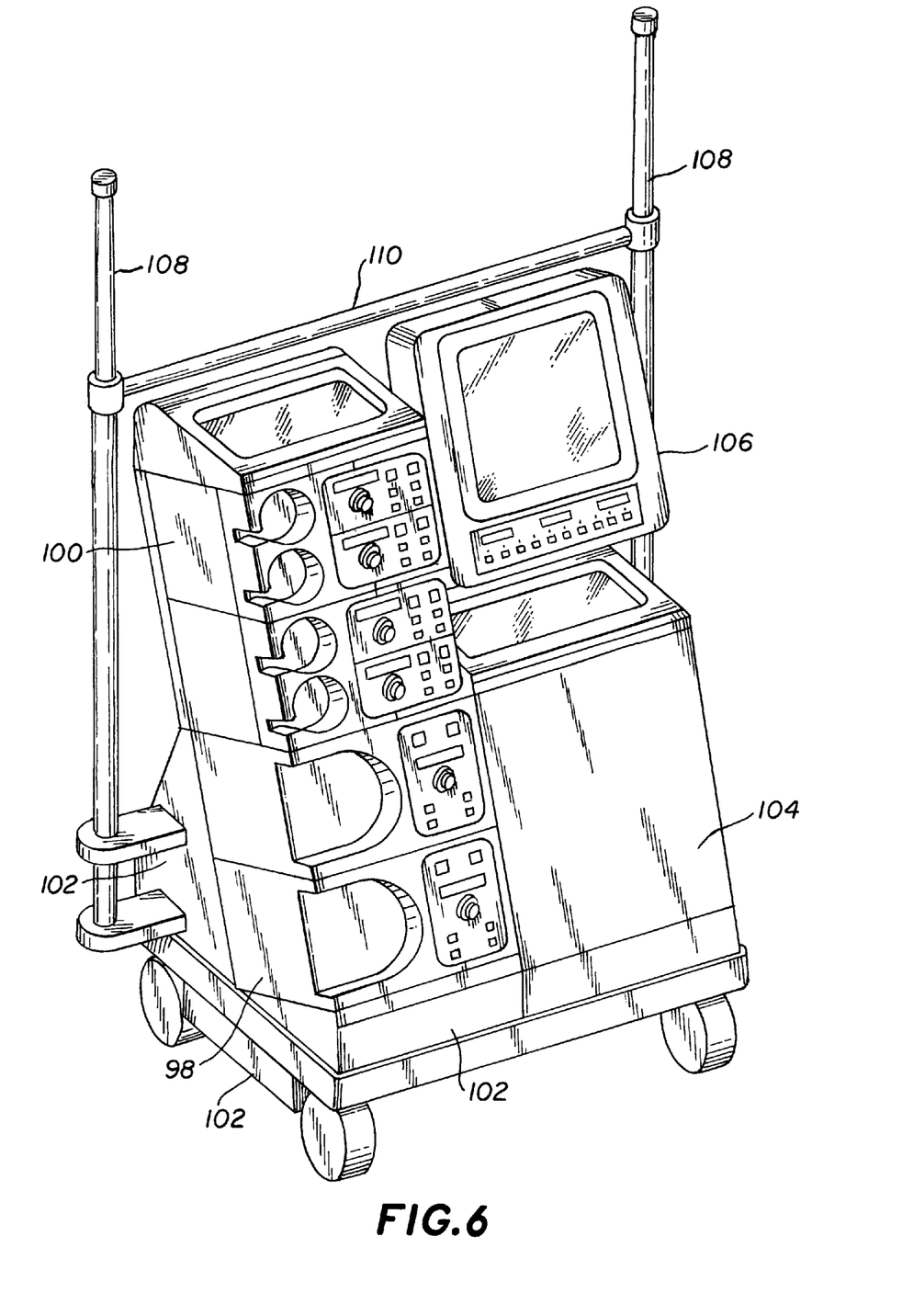
FIG. 6 is a pictorial view of a single stack alternative embodiment of the subject invention.

An alternative embodiment which retains the advantages of the canted front surface of the stack as discussed herein relative to FIG. 3, but is not limited to a centralized oxygenator design is illustrated in FIG. 6. This apparatus features two single-head pump assemblies 98 and two double-head assemblies 100. The controller functions are distributed throughout the console 102 and in the controller box 104. The display monitor 106 can be used for display of parameters or other information, and for input by the perfusionist. The masts 108 can be used to mount the oxygenator, the venous clamp, a light fixture, the crystalloid solution (none shown), etc., and the mounting crossbar 110 can be used to mount writing surfaces (not shown), etc. The dimensions of the apparatus of FIG. 6 are such that the perfusionist's view of the operating table is not obstructed.

As is evident from the foregoing description of the embodiments, the subject invention addresses several ergonomic issues, thereby improving perfusionist efficiency. Improved perfusionist efficiency makes it easier for the perfusionist to contribute positively to patient outcomes. Because the flanking units and tubing are plainly visible from a single position, they can be monitored by the perfusionist without losing peripheral sight of the oxygenator assembly 20. The improved visibility of all tubing facilitates rapid reaction by the perfusionist to air, kinks or occlusions observed in the tubing. The subject apparatus provides a highly organized tubing arrangement, facilitating pre-surgical set-up. The embodiments of FIGS. 3 and 5 also facilitate perfusionist detection of tubing or pump head damage. The canted instrumentation panel of FIG. 3 further facilitates perfusionist identification of the origin of an alarm and the status of all control systems. Because the flanking units are arranged in two stacks or cascades instead of one, the perfusionist can have a clear view of the operating table, operating room monitors and/or surgical team without moving. This permits the perfusionist to respond rapidly to patient data on monitors and to surgical team actions or communications.

The patient can benefit from the subject invention in several ways. Because the extracorporeal volume may be lessened, hemodilution and pharmaceuticals may be minimized and systemic perfusion may be maximized. Dependence on banked blood may be reduced, thereby reducing the risk of blood-borne disease. Because the perfusionist can survey all components of the assembly rapidly, he can respond quickly to changing patient or equipment conditions. These benefits may facilitate a positive influence on faster patient recovery and reduced health care costs.

Many functional details of the foregoing embodiments have been described in detail. It will be appreciated by those skilled in the art that many variations of these functional details are possible without departing from the spirit of the present invention.

All references cited herein are incorporated in their entirety by reference herein.

What is claimed is:

1. A perfusion assembly for extracorporeal transfer of fluids, comprising:
    a console;
    at least two flanking units which are atop said console, said flanking units comprising at least one pump assembly and at least one of a pump assembly, a parameter monitoring assembly, a display monitor or a controller; and
    a central cavity adapted to receive an oxygenator, said cavity being between said at least two flanking units atop said console.

2. The assembly of claim 1, further comprising an oxygenator in said central cavity.

3. The assembly of claim 1, further comprising a reservoir in said central cavity.

4. The assembly of claim 3, wherein said reservoir is one or a combination of a cardiopulmonary reservoir, a cardiotomy reservoir or a vent circuit reservoir.

5. The assembly of claim 1, further comprising a heat exchanger in said central cavity.

6. The assembly of claim 1, wherein the flanking units are detachable from said console and positionally interchangeable.

7. The assembly of claim 1, wherein said console is substantially rectangular.

8. The assembly of claim 1, wherein said console is substantially V-shaped.

9. The assembly of claim 1, wherein said console is substantially U-shaped.

10. The assembly of claim 1, wherein the console comprises at least two peripheral segments and a central segment, said central segment positioned below the central cavity.

11. The assembly of claim 10, wherein said central segment comprises a console crossbar located below and in front of the central cavity.

12. The assembly of claim 10, wherein a joint between the central segment and peripheral segment is hinged, whereby the segment can be rotated about the hinged joint axis.

13. The assembly of claim 10, wherein the central segment is adjustable in length.

14. The assembly of claim 1, comprising at least three flanking units, wherein said units in excess of a first and a second unit are vertically stacked on said first and second units to create stacks.

15. The assembly of claim 14, wherein said stacked units are canted and offset from units immediately below, whereby front surfaces of said stacks slant toward a back surface of the assembly as the stacks ascend.

16. The assembly of claim 1, wherein the flanking units are positioned on sets of steps which rise from a front surface to a back surface of said console, said sets of steps flanking the central cavity.

17. The assembly of claim 2, wherein at least two flanking units are pump assemblies which are positioned to be radially equidistant from the oxygenator longitudinal axis.

18. The assembly of claim 1, further comprising a mounting fixture.

19. The assembly of claim 18, wherein said mounting fixture comprises a mast.

20. The assembly of claim 19, wherein said mounting fixture further comprises a mounting crossbar.

21. The assembly of claim 20, wherein said mounting crossbar is adjustable in length.

22. The assembly of claim 1, wherein a controller is in electrical communication with at least one of the pump assembly, a parameter monitoring assembly and a display monitor.

23. The assembly of claim 1, wherein said pump assembly comprises:
   an instrumentation panel for optional local controlling or monitoring of a pumping means; and
   a housing comprising the pumping means, said housing and panel in electrical communication for processing electrical signals indicative of pumping means.

24. The pumping assembly of claim 1, wherein said pumping assembly comprises at least one of a cardiopulmonary pump, a cardioplegia pump, a left ventricular vent pump, or a cardiotomy pump.

25. The assembly of claim 23, wherein the pumping means is under local control of the instrumentation panel.

26. The assembly of claim 23, wherein the pumping means is under control of the controller, and at least one flanking unit comprises the controller.

27. The assembly of claim 23, wherein at least one flanking unit comprise a controller and, the pumping means is under the control of the controller.

28. The assembly of claim 1, wherein at least one flanking unit comprises a display monitor.

29. The assembly of claim 1, wherein a display monitor is mounted on a mounting fixture and no flanking unit comprises a display monitor.

30. The assembly of claim 1, wherein one flanking unit comprises a parameter monitoring assembly and said parameter monitoring assembly performs at least one of the functions of sensing, monitoring or regulating temperature, pressure, pH, blood gases, venous oxygen saturation, arterial oxygen saturation, reservoir blood level, hematocrit, arterial line air bubbles, cardioplegia delivery line air bubbles, electrolytes, anticoagulation time, hemoglobin, venous clamp, or composition of oxygenator feed gas.

31. The assembly of claim 2, further comprising a venous line in fluid communication with the oxygenator an arterial line in fluid communication with the oxygenator, a crystalloid solution supply line in fluid communication with a crystalloid solution supply bag, a cardioplegia blood line in fluid communication with the oxygenator and the crystalloid solution supply line, a cardioplegia delivery line in fluid communication with the crystalloid solution supply line and the cardioplegia blood line, a ventricular vent line in fluid communication with the oxygenator, and a cardiotomy line in fluid communication with one of a waste bag or the oxygenator.

32. The assembly of claim 31, wherein said fluid communications between said venous line and oxygenator, between said ventricular vent line and said oxygenator, and said cardiotomy line and said oxygenator comprise a single reservoir.

33. The assembly of claim 31, further comprising an air bubble sensor disposed in at least one of the arterial line or cardioplegia delivery line.

34. The assembly of claim 31, further comprising a pressure sensor in at least one of said venous, arterial, cardioplegia or vent lines.

35. The assembly of claim 31, further comprising a temperature sensor in at least one of said venous, arterial or cardioplegia lines.

36. The assembly of claim 3, further comprising at least one of a fluid level detector and a temperature sensor.

37. A perfusion assembly for extracorporeal transfer of fluids, comprising:
   a console;
   at least two flanking units which are atop said console, said flanking units comprising at least one pump assembly and at least one of a pump assembly, a parameter monitoring assembly, a display monitor or a controller;
   a central cavity adapted to receive an oxygenator, said cavity being between said at least two flanking units atop said console; and
   a tubing assembly adapted for use in the perfusion assembly.

38. The perfusion assembly of claim 37, wherein said tubing assembly comprises a cardiopulmonary circuit.

39. The perfusion assembly of claim 35, wherein said cardiopulmonary circuit comprises a venous line, an oxygenator, and an arterial line.

40. The perfusion assembly of claim 39, wherein said cardiopulmonary circuit further comprises a cardiopulmonary loop and a reservoir.

41. The perfusion assembly of claim 39, wherein said cardiopulmonary circuit further comprises a heat exchanger.

42. The perfusion assembly of claim 37, wherein said tubing assembly comprises a cardioplegia circuit.

43. The perfusion assembly of claim 42, wherein said cardioplegia circuit comprises a crystalloid solution supply line, a cardioplegia blood line and a cardioplegia delivery line.

44. The perfusion assembly of claim 37, wherein said tubing assembly comprises a cardiotomy line.

45. The perfusion assembly of claim 37, wherein said tubing assembly comprises a ventricular vent line.

* * * * *